US009581573B2

(12) United States Patent
Aota et al.

(10) Patent No.: US 9,581,573 B2
(45) Date of Patent: Feb. 28, 2017

(54) LIQUID CHROMATOGRAPH (71) Applicant: HITACHI HIGH-TECHNOLOGIES CORPORATION, Tokyo (JP)

(72) Inventors: Toshimichi Aota, Tokyo (JP); Masahito Ito, Tokyo (JP); Chihiro Yoshioka, Tokyo (JP); Takaaki Suzuki, Tokyo (JP); Peter Grosshans, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/646,509

(22) PCT Filed: Nov. 11, 2013

(86) PCT No.: PCT/JP2013/080465
§ 371 (c)(1),
(2) Date: May 21, 2015

(87) PCT Pub. No.: WO2014/087812
PCT Pub. Date: Jun. 12, 2014

(65) Prior Publication Data
US 2015/0293064 A1 Oct. 15, 2015

(30) Foreign Application Priority Data
Dec. 6, 2012 (JP) ................................. 2012-267618

(51) Int. Cl.
*G01N 30/34* (2006.01)
*G01N 30/86* (2006.01)
(52) U.S. Cl.
CPC .............. *G01N 30/34* (2013.01); *G01N 30/86* (2013.01); *G01N 30/8658* (2013.01)
(58) Field of Classification Search
None
See application file for complete search history.

(56) References Cited

U.S. PATENT DOCUMENTS

| | | | | |
|---|---|---|---|---|
| 5,970,425 A | * | 10/1999 | Ono ........................ | G01N 30/88 702/183 |
| 2003/0110000 A1 | * | 6/2003 | Quimby ............. | G01N 30/8665 702/89 |
| 2009/0090173 A1 | * | 4/2009 | Fukuda .................. | G01N 30/34 73/61.55 |

FOREIGN PATENT DOCUMENTS

| | | |
|---|---|---|
| JP | 05-142222 A | 6/1993 |
| JP | 6-201674 A | 7/1994 |

(Continued)

OTHER PUBLICATIONS

International Preliminary Report on Patentability received in corresponding International Application No. PCT/JP2013/080465 dated Jun. 18, 2015.

(Continued)

*Primary Examiner* — Paul West
*Assistant Examiner* — Mark A Shabman
(74) *Attorney, Agent, or Firm* — Mattingly & Malur, PC (57) ABSTRACT

A liquid chromatograph includes a liquid chromatograph unit that has a pump sending an eluent to a detector and a control unit that controls the liquid to be sent by the pump based on a predetermined time table. The control unit stores an elution response of the liquid chromatograph unit which is obtained when a predetermined command value is input and another elution response which is obtained when the same command value is input to another liquid chromatograph. The time table is converted in the control unit based on the elution response and the other elution response to obtain respective elution profiles. In this manner, even when a measuring method related to another liquid chromatograph is used, it is possible to provide a liquid chromatograph capable of obtaining measurement results which are the same as those obtained when the measuring method is used in the other liquid chromatograph.

20 Claims, 9 Drawing Sheets

(56) References Cited

FOREIGN PATENT DOCUMENTS

| | | |
|---|---|---|
| JP | 2006-201064 A | 8/2006 |
| JP | 2009-281897 A | 12/2009 |

OTHER PUBLICATIONS

International Search Report of PCT/JP2013/080465.

\* cited by examiner

| Time (min) | %A | %B | Flow (ml/min) |
|---|---|---|---|
| 0.0 | 90 | 10 | 1 |
| 5.0 | 90 | 10 | 1 |
| 5.1 | 50 | 50 | 1 |
| 10.0 | 50 | 50 | 1 |
| 10.1 | 10 | 90 | 1 |
| 15 | 10 | 90 | 1 |
| 15.1 | 90 | 10 | 1 |
| 20 | 90 | 10 | 1 |

LIQUID CHROMATOGRAPH

TECHNICAL FIELD

The present invention relates to a liquid chromatograph and particularly relates to system conversion in a plurality of liquid chromatographs.

BACKGROUND ART

An analytical technique using a liquid chromatograph needs to be highly accurate. A measuring method can be exemplified as contents to be set in the liquid chromatograph when a chromatogram is measured. The measuring method can be defined as, for example, the flow rate of an eluent (solvent), the sample injection amount, and the upper limit of the pressure.

Patent Literature 1 discloses a technique for converting a measuring method of a certain device (conventional liquid chromatograph) to a measuring method of another device (ultrahigh velocity liquid chromatograph) with linear velocity (velocity at which a certain component passes through a column) which is higher than that of the device. Further, Patent Literature 1 discloses that the correction value is acquired using data or the like of the column at the time of conversion of the measuring method.

CITATION LIST

Patent Literature

PTL 1: JP-A-2009-281897

SUMMARY OF INVENTION

Technical Problem

However, in a case where the same measuring method is used in liquid chromatographs which are different from each other, the retention time or the degree of separation of the chromatograms may vary due to a difference among various specifications in the two devices (for example, differences between tube diameters, dead volumes of pumps, liquid mixing performance of mixers, dead volumes of samplers, sample diffusion capacities other than columns, and detectors).

On the contrary, for example, a user who introduces a new liquid chromatograph for pharmaceutical development or the like wants to obtain the same measurement results as those of a device in the related art without developing a new measuring method even when the new device is used in many cases.

For this reason, problems in which (1) a measuring method needs to be developed for each liquid chromatograph, (2) a measuring method in the related art cannot be used at the time of switching a liquid chromatograph with another device, and (3) a plurality of liquid chromatograms are required for each measuring method cannot be solved with the technique in the related art.

The present invention has been made in consideration of solving the above-described problems, and an object thereof is to provide, even when a measuring method related to another liquid chromatograph is used, a liquid chromatograph capable of obtaining measurement results which are the same as those obtained when the measuring method related to another liquid chromatograph is used.

Solution to Problem

According to the present invention, in order to achieve the above-described object, there is provided a liquid chromatograph including: a liquid chromatograph unit that includes an elution unit sending an eluent to a detecting unit; and a control unit that controls a liquid to be sent by the elution unit based on a predetermined time table, in which the control unit stores an elution response of the liquid chromatograph unit which is obtained when a predetermined command value is input to the elution unit and an elution response of another liquid chromatograph which is obtained when the command value is input to another elution unit in another liquid chromatograph.

Advantageous Effects of Invention

According to the present invention, a measuring method related to one device can be used in another device and thus the measuring method can be seamlessly transferred between devices.

DESCRIPTION OF EMBODIMENTS

Hereinafter, embodiments of the present invention will be described with reference to the accompanying drawings.

Figure 1:
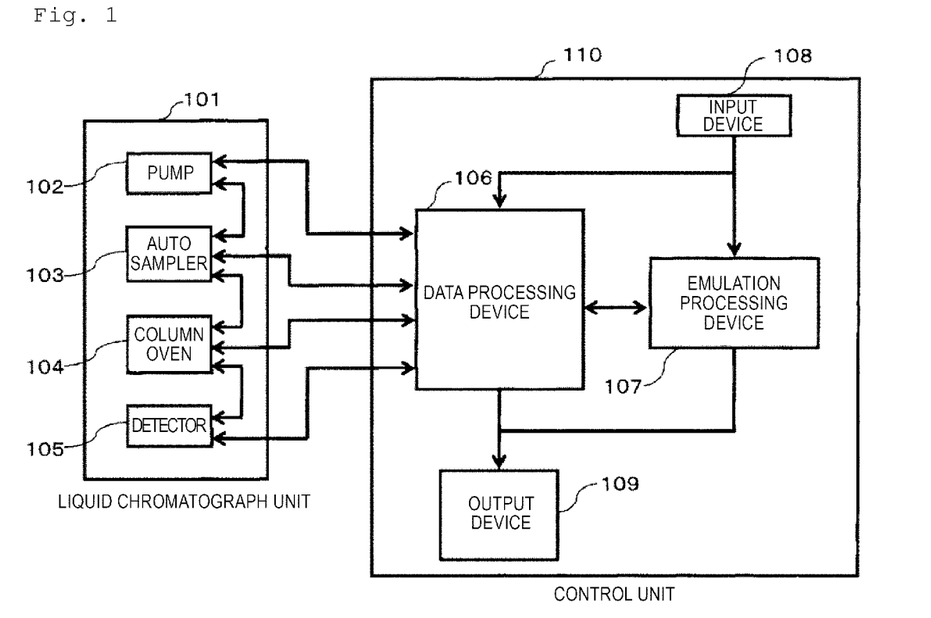
FIG. 1 is a system configuration diagram of a liquid chromatograph according to an embodiment of the present invention.

FIG. 1 is a system configuration diagram of a liquid chromatograph according to an embodiment of the present invention. The liquid chromatograph illustrated in the figure includes a liquid chromatograph unit 101 in which separation and analysis of a mixed sample are performed and a control unit 110 which is a control device for controlling each device related to the liquid chromatograph unit 101 based on a predetermined measuring method.

The liquid chromatograph unit 101 includes a pump (elution unit) 102 that sends an eluent based on a command from the control unit 110; an auto sampler (sample injection unit) 103 that injects a sample with respect to an eluent from the pump 102 based on a command from the control unit 110; a column oven (separating unit) 104 that holds the temperature of a column 207 (see FIG. 2) based on a command from the control unit 110; and a detector (detecting unit) 105 that detects a component eluted from the column 207 and converts the component into an electrical signal to be output to the control unit 110.

The control unit 110 includes a data processing device 106 that transceives commands and data among respective devices related to the liquid chromatograph unit 101; an input device (for example, a pointing device, a keyboard, and a tablet) 108 to which a command or the like from an operator is input; an emulation processing device 107 that performs a process (system conversion process) of converting a measuring method input through the input device 108; and an output device 109 on which detection results of a detector 105 and a graphical user interface (GUI) related to various operations of the liquid chromatograph unit 101 and the control unit 110 are shown. Measurement values of each component detected by the detector 105 are taken in the data processing device 106 and analysis results of samples are transmitted to and displayed on the output device 109.

In the measuring method, data columns (hereinafter, also referred to as a "time table" or "elution time table") which are time series of control command values (target values of the elution profile) to the pump 102 and in which a time change of the elution profile of an eluent due to the pump 102 is determined in advance are included. Examples of elution profiles include the flow rate and the pressure of an eluent and the mixing ratio of respective eluents in a predetermined flow rate in a case where a plurality of eluents are present. Specific examples of the time table of the pump 102 will be described below. In the present embodiment, system conversion will be described by exemplifying a case where measurement in another liquid chromatograph is reproduced by converting the time table of the pump 102. As described below, the emulation processing device 107 performs conversion of the time table (system conversion) based on a difference between elution response of respective liquid chromatographs such that the "elution profile" shown when the same time table is used in another liquid chromatograph is actually shown in the liquid chromatograph of the present embodiment.

The elution response indicates an actual elution profile of each liquid chromatograph obtained when a predetermined command value (specific examples of the command value will be described below) is input to the pump 102. For example, in a case where the same command value is input to a plurality of liquid chromatographs, the elution profiles vary due to a difference among various specifications (for example, differences between tube diameters, dead volumes of pumps, liquid mixing performance of mixers, dead volumes of samplers, sample diffusion capacities other than columns, and detectors) in the plurality of liquid chromatographs. That is, an elution response becomes an intrinsic value of each liquid chromatograph.

As a method of measuring an actual elution profile (elution response), a method of measuring absorbance of an eluent sent by the pump 102 based on a predetermined command value can be exemplified. The detector 105 installed in the liquid chromatograph unit 101 can be used as means for measuring the absorbance of an eluent.

In addition, it is preferable that command values input to pumps of respective liquid chromatographs when elution responses are acquired are the same as each other, but the command values may be the same within the range of resolution of the detector 105 and may not be perfectly matched if the detection results of the detector 105 are finally the same. That is, the command values may be the same within the range of the resolution of the detector 105 or the like and respective command values are regarded as the same as each other when the command values are within the above-described range in the present application.

Figure 2:
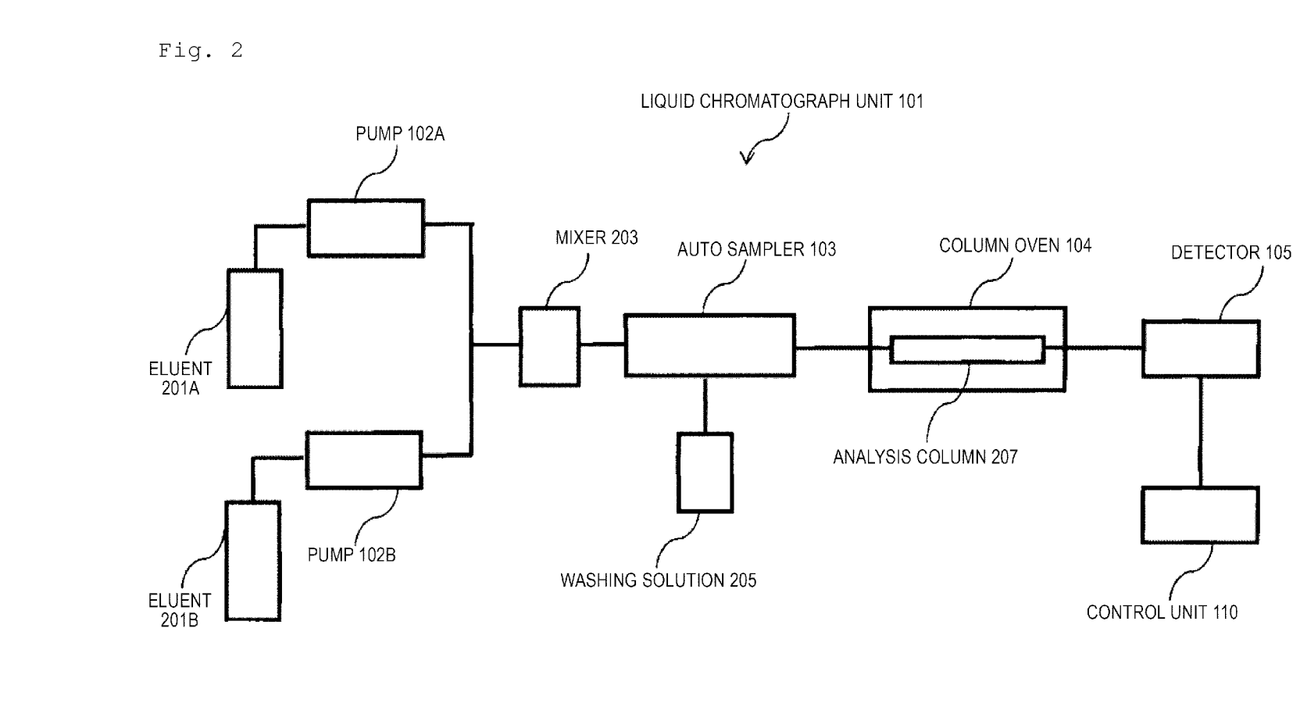
FIG. 2 is a system configuration diagram of a liquid chromatograph unit 101 according to an embodiment of the present invention.

FIG. 2 illustrates a system configuration diagram of the liquid chromatograph unit 101 according to the embodiment of the present invention. In addition, the same elements in the figure described above are denoted by the same reference numerals and the description thereof is not repeated (the same applies hereinafter). The liquid chromatograph unit 101 illustrated in the figure includes the pumps 102 (a pump 102A sending out an eluent 201A and a pump 102B sending out an eluent 201B), a mixer 203, the auto sampler 103, the column oven 104, and the detector 105.

The pumps 102A and 102B pump up the eluents 201A and 201B based on the contents of the time table stored in the data processing device 106. The eluents sent from the pumps 102A and 102B are mixed by the mixer 203 and then sent to the column oven 104 through the auto sampler 103. A sample is injected from the auto sampler 103 and sent to the analysis column 207. The detector 105 detects sample components having passed through the column 207 and the detection results are stored in a storage device of the data processing device 106 of the control unit 110.

Figure 3:
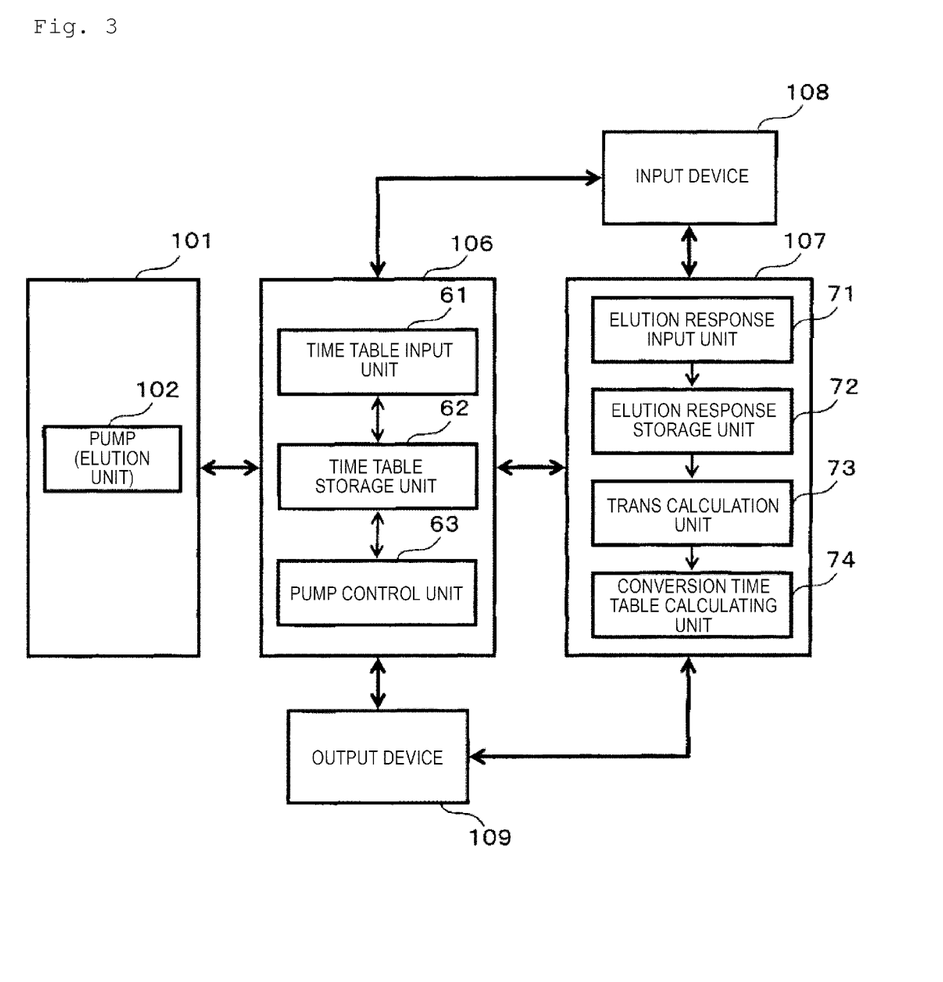
FIG. 3 illustrates a part of a system configuration diagram of a data processing device 106 and an emulation processing device 107 according to an embodiment of the present invention.

FIG. 3 illustrates a part of the system configuration diagram of the data processing device 106 and the emulation processing device 107 according to the present embodiment of the present invention. Further, although not illustrated in the figure, the data processing device 106 and the emulation processing device 107 respectively include an arithmetic processing device (for example, a CPU) serving as arithmetic means for performing various programs; storage devices (for example, a semiconductor memory such as a ROM, a RAM, or a flash memory, and a magnetic storage device such as a hard disk drive) serving as storage means for storing the programs and various pieces of data; and an input and output arithmetic processing device for controlling input and output of data, commands, and the like to respective devices 101, 106, 107, 108, and 109.

In FIG. 3, the data processing device 106 includes a time table input unit 61, a time table storage unit 62, and a pump control unit 63.

The time table input unit 61 is a portion to which a time table related to the control of the pumps 102 (pumps 102A and 102B) is input from the outside. Examples of the method of inputting the time table include a method of inputting the time table through a storage medium in which the time table is stored and a method of inputting the time table using communication through another computer in which the time table is stored and a network in addition to a method of inputting the time table using the input device 108.

The time table storage unit 62 is a portion in which a time table input through the time table input unit 61 and a time table manipulated (converted) by a conversion time table manipulating unit 74 in the emulation processing device 107, which will be described below, are stored. Here, the time table input through the time table input unit 61 will be described with reference to the drawings.

Figure 4:
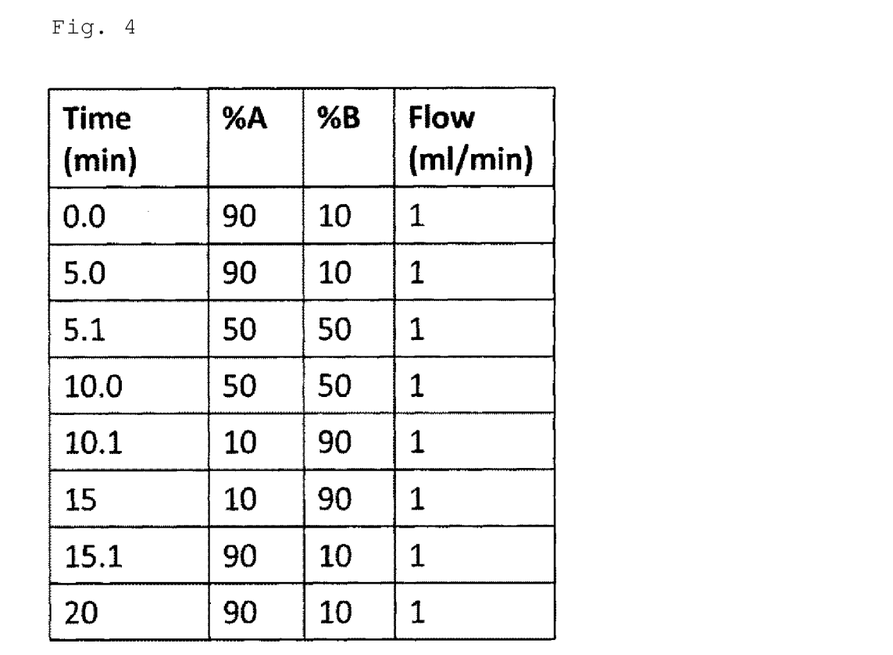
FIG. 4 is a diagram illustrating an example of a time table related to control of a pump of a liquid chromatograph according to an embodiment of the present invention.
Figure 5:
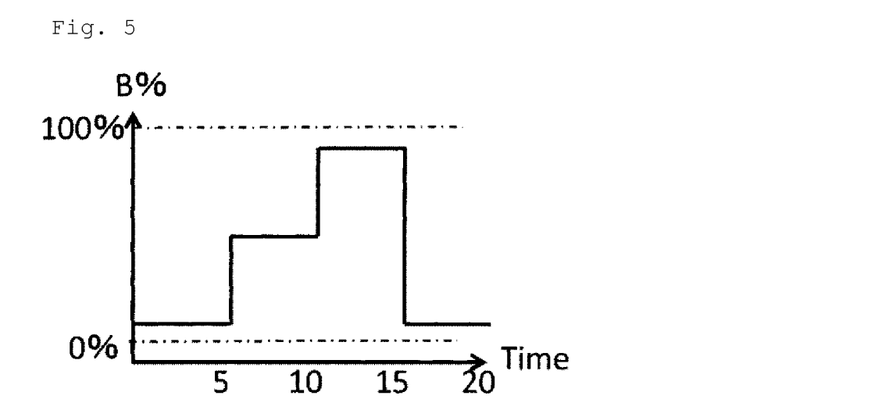
FIG. 5 is a diagram illustrating the time table of FIG. 4 using a graph.

FIG. 4 is a diagram illustrating an example of a time table (elution time table) related to the control of a pump of the liquid chromatograph illustrated in FIG. 2 and FIG. 5 is a diagram illustrating the time table of FIG. 4 using a graph. In the time table of FIG. 4, "% A" indicates the composition ratio of the eluent 201A (pump 102A) to a moving layer and "% B" indicates the composition ratio of the eluent 201B (pump 102B) to the moving layer. The total flow rate of the eluents A and B is constantly held at 1 [mL/min]. In addition, "B %" in the graph of FIG. 5 indicates the composition ratio of the eluent 201B to the moving layer. As understood from the graph of FIG. 5, a stepwise method in which the ratio of an eluent is changed in a stepwise manner is used here.

Figure 6:
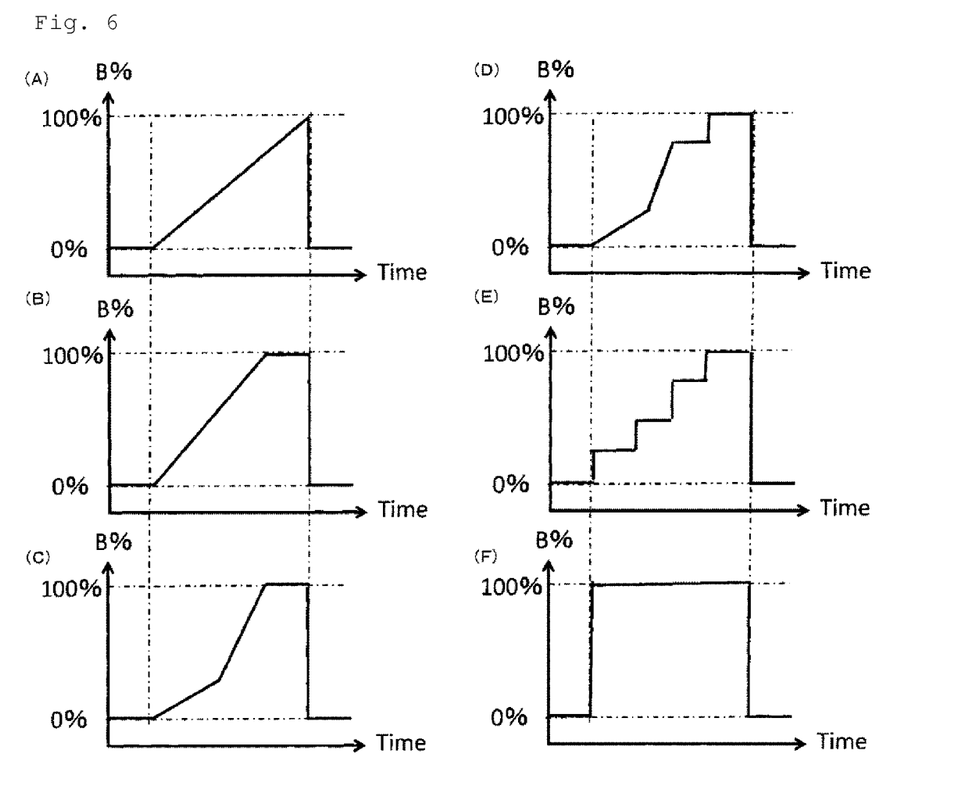
FIG. 6 illustrates other examples of the time table (format of a graph) related to control of a pump of a liquid chromatograph according to an embodiment of the present invention.

In addition, the time table which can be used in the present invention is not limited to the time tables illustrated in FIGS. 4 and 5. FIG. 6 illustrates other examples of the time table (graph) related to control of the pump of the liquid chromatograph illustrated in FIG. 2. As the time table, various time tables (for example, gradient and isocratic) illustrated in A to F in FIG. 6 and the like can be used. Further, a case where two kinds of eluents are mixed with two pumps is described here, but three kinds or more eluents may be mixed with two pumps and a plurality of eluents may be mixed with one pump. Various time tables can be used according to the number of pumps and the kinds of eluents.

Returning to FIG. 3, the pump control unit 63 is a portion that controls the pumps 102 (pumps 102A and 102B) of the liquid chromatograph unit 101 based on the time table stored in the time table storage unit 62. In a case where a time table to which the conversion time table calculating unit 74 is converted is selected as a time table used for the pump control unit 63, the pump control unit 63 controls the pumps 102 based on the time table.

In FIG. 3, the emulation processing device 107 includes an elution response input unit 71, an elution response storage unit 72, a trans calculation unit 73, and the conversion time table calculating unit 74.

The elution response input unit 71 is a portion to which elution responses of a plurality of liquid chromatographs including the liquid chromatograph unit 101 are input. Examples of the method of inputting elution responses to the input unit 71 include a method of inputting the elution responses through a storage medium in which the elution responses are stored and a method of inputting the elution responses using communication through another computer in which the elution responses are stored and a network in addition to a method of inputting the elution responses using the input device 108.

The elution response storage unit 72 is a portion in which the elution responses of a plurality of liquid chromatographs (including the liquid chromatograph unit 101) input through the elution response input unit 71 are stored.

The trans calculation unit 73 is a portion that calculates a difference (Trans(t)) between elution responses of the liquid chromatograph unit 101 and another liquid chromatograph. The contents of the calculation will be described below.

The conversion time table calculating unit 74 is a portion that converts a time table which is stored in the time table storage unit 62 and used for sample analysis based on the difference of the elusion response calculated by the trans calculation unit 73. A time table which is a target to be converted is input to the conversion time table calculating unit 74 from the time table storage unit 62. As a case where a time table is converted by the conversion time table calculating unit 74, a case where measurement results obtained in a certain device (liquid chromatograph A) using a predetermined time table are reproduced in another device (liquid chromatograph B) can be exemplified. A specific conversion process of a time table using the conversion time table calculating unit 74 will be described below. A time table converted by the conversion time table calculating unit 74 is input to and stored in the time table storage unit 62 of the data processing device 106.

Figure 7:
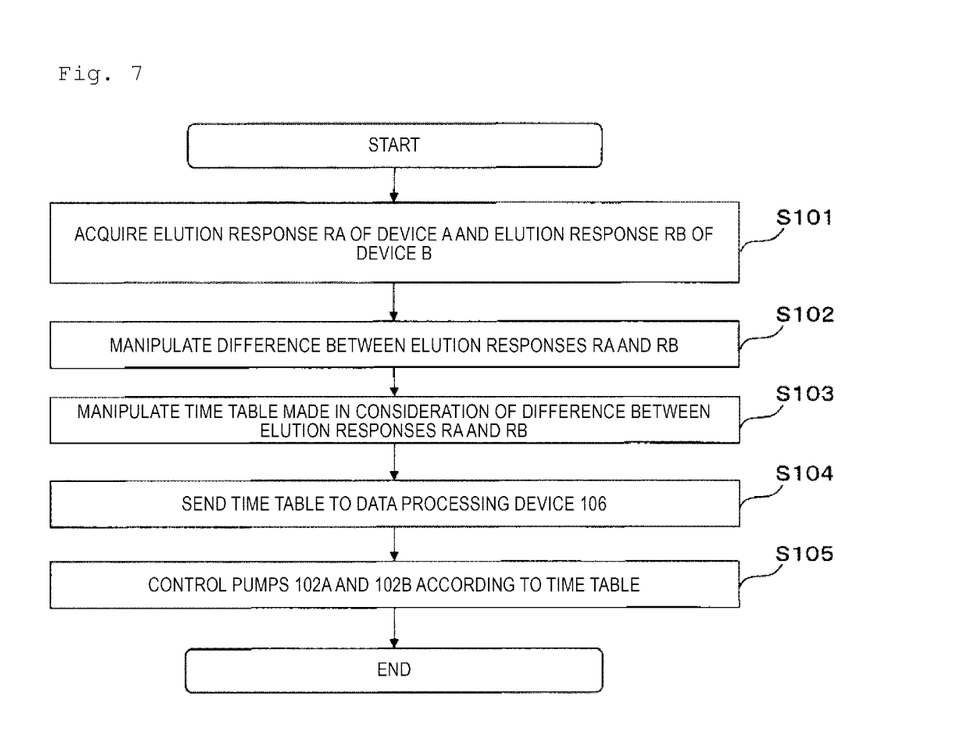
FIG. 7 is a flowchart of system conversion performed by a liquid chromatograph according to an embodiment of the present invention.

FIG. 7 is a flowchart of system conversion using the liquid chromatograph according to the embodiment of the present invention. A method of controlling a liquid using system conversion (time table conversion of the pumps 102A and 102B) will be described below with reference to this figure. Here, under the assumption of the two liquid chromatographs A and B which are different from each other and a common time table related to control of pumps of the liquid chromatographs A and B, a case of performing system conversion of the liquid chromatograph B such that measurement results obtained when the pump is controlled by the liquid chromatograph B based on the time table approach measurement results obtained when the pump is controlled by the liquid chromatograph A based on the time table will be described. Here, the description will be made under the assumption that the liquid chromatograph B corresponds to a liquid chromatograph illustrated in FIGS. 1 and 2 and the liquid chromatograph A has the same configuration as that illustrated in at least FIG. 2.

In FIG. 7, first, the emulation processing device 107 acquires elution responses of the liquid chromatograph A and the liquid chromatograph B through the elution response input unit 71 and stores the elution responses in the elution response storage unit 72 (S101). The elution responses of the liquid chromatograph A and the liquid chromatograph B are derived from respective tube diameters, the dead volumes of the pumps 102A and 102B, liquid mixing performance of the mixers 203, the dead volumes of the samplers 103, sample diffusion capacities other than columns, and the detectors 105. Here, the elution response of the liquid chromatograph A is set as RA and the elution response of the liquid chromatograph B is set as RB.

The elution responses RA and RB are obtained by measuring actual elution profiles (for example, impulse responses) of respective liquid chromatographs A and B when the same command value (for example, impulse input) is input to the pumps 101A and 101B of the liquid chromatographs A and B. The elution responses (actual elution responses) of the liquid chromatographs A and B can be acquired by measuring the absorbance of the eluent sent through the pumps 102A and 102B and the mixer 203 using the detectors 105 of respective devices A and B. The elution responses RA and RB acquired in this manner are stored in the elution response storage unit 72 through the input device 108 or the like.

Meanwhile, the measurement results (actual elution profiles of the eluents) when the pumps 102A and 102B are controlled are represented by the following equations (1) and (2) using elution responses RA(t) and RB(t) based on the time tables (that is, the time change in a mixing ratio of the eluent 201A to the eluent 201B) illustrated in FIGS. 4 to 6 in the liquid chromatographs A and B. Moreover, the actual elution profiles of the eluents can be acquired by measuring the absorbance of the eluents using the detector 105 in the same manner as that of the elution responses. Further, in the following equations, the elution responses RA and RB can be suitably represented by functions (RA(t) and RB(t)) of a time t and "*" indicates a convolution operation.

[Math. 1]

$$A = \text{TimeTable} * RA(t) \quad \text{Equation (1)}$$

Measurement result of liquid chromatograph

[Math. 2]

$$B = \text{TimeTable} * RB(t) \quad \text{Equation (2)}$$

Measurement result of liquid chromatograph

As obvious from the equations (1) and (2), in a case where the same time table is input to respective liquid chromatographs A and B, the difference between the elution responses RA and RB of respective liquid chromatographs A and B becomes a difference between measurement results.

When the process of S101 ends, the emulation processing device 107 acquires a difference (Trans(t)) between the elution responses RA and RB of the liquid chromatographs A and B using the trans calculation unit 73 (S102). Since the equation (1) becomes equivalent to an equation obtained by convoluting the equation (2) with Trans(t), the following equation (3) is satisfied.

[Math. 3]

$$RA(t) = RB(t) * \text{Trans}(t) = \int_{-\infty}^{\infty} RB(t') \cdot \text{Trans}(t-t') dt' \quad \text{Equation (3)}$$

Here, the difference (Trans(t)) of the elution responses of the liquid chromatographs A and B can be manipulated through a data convolution operation of the equation (3). Therefore, the time table (TimeTableB(t)) for obtaining the same measurement results in the liquid chromatograph B as those in the liquid chromatograph A can be manipulated with the following equation (4) using the original time table (TimeTableB(t)) and Trans(t). In this manner, the conversion time table calculating unit 74 of the emulation processing device 107 reads the time table (TimeTableB(t)) which is a target to be converted from the time table storage unit 62 and the time table (TimeTableB(t)) made in consideration of the difference between the elution responses RA and RB of the liquid chromatographs A and B is manipulated based on the equation (4) (S103).

[Math. 4]

$$\text{TimeTable}B(t) = \text{TimeTable}A(t) * \text{Trans}(t) = \int_{-\infty}^{\infty} \text{TimeTable}A(t') \cdot \text{Trans}(t-t') dt' \quad \text{Equation (4)}$$

The conversion time table calculating unit 74 outputs the time table (converted time table: TimeTableB(t)) manipulated in S103 to the time table storage unit 62 of the data processing device 106 (S104). The pump control unit 63 of the data processing device 106 controls the pumps 102A and 102B based on the time table (TimeTableB(t)) (S105).

In this manner, since the time table (TimeTableB(t)) necessary for obtaining the same measurement results in the liquid chromatograph B as those in the liquid chromatograph A can be shown with the difference (Trans(t)) between elution responses of the liquid chromatographs A and B and the convolution of the existing time table (TimeTableA(t)), the same measurement results as those in the liquid chromatograph A can be obtained in the liquid chromatograph B using the existing time table (TimeTableA(t)) only by manipulating the difference (Trans(t)) between elution responses. That is, according to the present invention, since a time table can be diverted between liquid chromatographs and thus there is no need to separately perform development for using an existing time table related to one liquid chromatograph in another liquid chromatograph, the cost for development and the period for development can be reduced. Further, since the measuring method can be seamlessly transferred between liquid chromatographs when a time table is used in both the liquid chromatographs, a measuring method for plural types of liquid chromatographs can be developed in one liquid chromatograph. Further, since each time table (each measuring method) does not need to be used for plural liquid chromatographs, the cost for maintenance of a liquid chromatograph can be reduced and the necessity of securing a storage location of a device can be markedly reduced.

Next, an operation of the liquid chromatograph according to the present embodiment based on a screen displayed on the output device 109 will be described.

Figure 8:
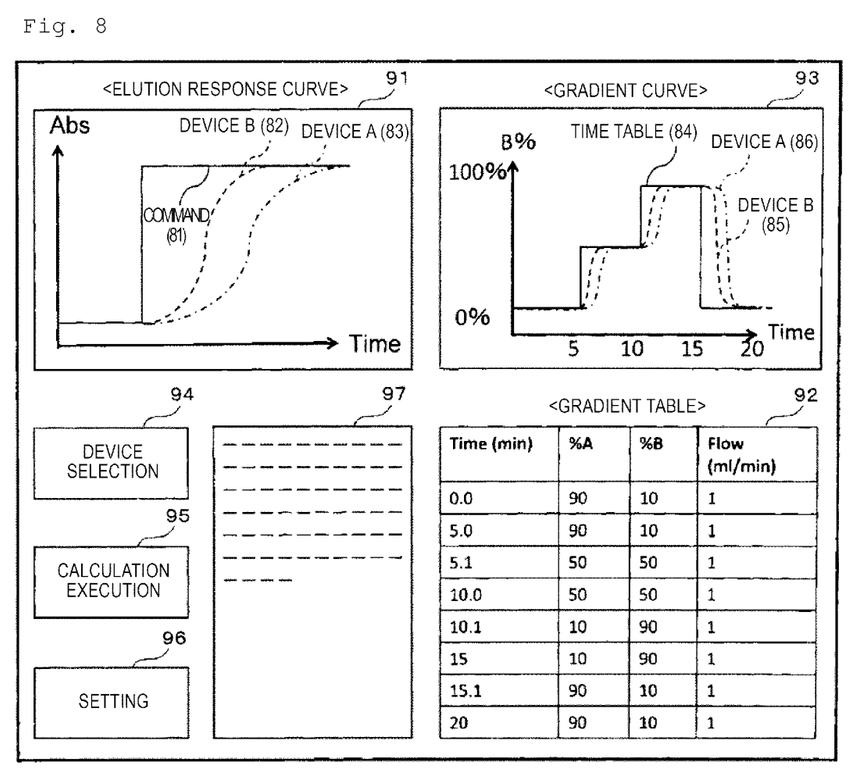
FIG. 8 is a diagram illustrating a display screen of an output device 109 according to an embodiment of the present invention.

FIG. 8 is a diagram illustrating a display screen of the output device 109 according to the present embodiment. An elution response curve display unit 91, a gradient table display unit 92, a gradient curve display unit 93, a device selection button 94, a calculation execution button 95, a setting button 96, and a message display unit 97 are provided on the display screen illustrated in the figure.

The elution response curve display unit 91 is a portion on which a command value 81 used for measuring an elution response, an elution response 82 by itself (liquid chromatograph B), and an elution response 83 of another device (liquid chromatograph A) which is a target reproducing measurement results are displayed. Elution responses related to a liquid chromatograph selected through the device selection button 94 are displayed on the elution response 83 of another liquid chromatograph. In the illustrated example, it is understood that the command value 81 is stepwise and the liquid chromatograph B (elution response 82) responds more rapidly compared to the device A (elution response 83). In addition, the command value 81 is across the micro time in an order of several milliseconds to several seconds and specific examples of the command value 81 will be described below.

The gradient table display unit 92 is a portion on which a time table (that is, a time table before being converted by the conversion time table calculating unit 74) used for sample measurement is displayed. In the illustrated example, a time table which is the same as that illustrated in FIG. 4 is used and displayed. The time table being used for measurement may be newly set by being input to a table on the display screen of the output device 109 through the input device 108 or may be used by reading the existing time table from the time table storage unit 62.

The gradient curve display unit 93 is a portion on which a graph shape 84 of a time table displayed on the gradient table display unit 92; an actual elution profile (actual gradient curve) 85 when the liquid chromatograph B is controlled by itself based on the time table; and an actual elution profile (actual gradient curve) 86 at the time when measurement results of another device (liquid chromatograph A) are reproduced by itself based on a difference between the time table and the elution profile are displayed. In the illustrated example, the graph shape of the time table illustrated in FIG. 5, the actual elution profile at the time when the liquid chromatograph B is controlled by itself based on the time table, and the actual elution profile of another device (liquid chromatograph A) obtained by controlling the liquid chromatograph B by itself based on a time table which is converted are displayed.

The device selection button 94 is a button for selecting another device that reproduces measurement results. As a specific method of selecting a device, for example, when the device selection button 94 is pressed by the input device 108 such as a pointing device or the like, a plurality of device names in which elution responses are stored in the elution response storage unit 72 are displayed on a screen with a different window or the like and one of the devices is selected by the operator through the input device 108.

The calculation execution button 95 is a button for executing a process (S102) of manipulating a difference of elution responses between the device (liquid chromatograph A) selected through the device selection button 94 and itself (liquid chromatograph B) and a process (S103) of manipulating a time table made in consideration of the difference using the emulation processing device 107.

The setting button 96 is a button for outputting a time table (converted time table) manipulated by pressing of the calculation execution button 95 to the data processing device 106 (S104) and setting the time table to be used for control of the pump 102.

The message display unit 97 is a portion on which messages or the like related to the operation and the process of the liquid chromatograph are displayed.

Figure 9:
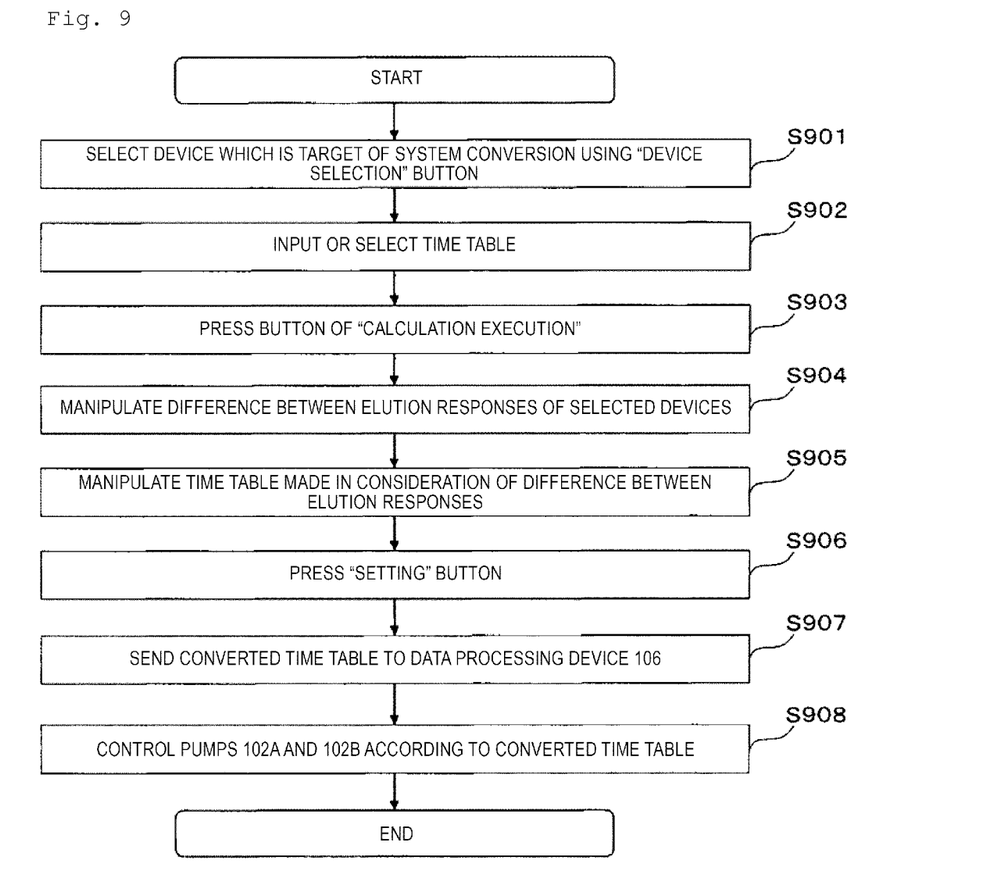
FIG. 9 is a flowchart of operation procedures and a process of a control unit 110 conforming with the operation procedures according to an embodiment of the present invention.

FIG. 9 is a flowchart of operation procedures and a process of the control unit 110 in conformity with the operation procedures.

The emulation processing device 107 stands by until the device selection button 94 is pressed by the operator. The operator presses the device selection button 94 through the input device 108 and selects another device that reproduces measurement results by itself (liquid chromatograph B) (S901). Here, the description is made under the assumption that the liquid chromatograph A is selected as another device.

When a target device is selected in S901, the emulation processing device 107 requests selection of a time table used for sample measurement through the message display unit 97 to the operator. In addition, the operator performs input or selection of the time table used for the sample measurement through the input device 108 (S902). The specific method of the input or the selection is as described above. In addition, the process of S902 can be omitted in a case where the time table to be used is determined in advance.

When the selection of the time table is completed, the emulation processing device 107 stands by until the calculation execution button 95 is pressed. At this time, the purport of requesting pressing of the calculation execution button 95 by the operator may be displayed on the message display unit 97.

When the calculation execution button 95 is pressed by the operation using the input device 108, the trans calculation unit 73 of the emulation processing device 107 performs a process of manipulating the difference between the elution responses of the device (liquid chromatograph A) selected in S901 and itself (liquid chromatograph B) (S904). The specific contents of the manipulating process at this time are the same as those of S102 described above. Further, the conversion time table calculating unit 74 of the emulation processing device 107 performs a process of manipulating the time table made in consideration of the difference which is manipulated in S904 (S905). The specific contents of the manipulating process at this time are the same as those of S103 described above.

When the process of manipulating the time table in S905 is completed, the emulation processing device 107 stands by until the setting button 96 is pressed. At this time, the purport of requesting pressing of the setting button 96 by the operator may be displayed on the message display unit 97.

When the setting button 96 is pressed by the operator using the input device 108, the emulation processing device 107 outputs the time table manipulated in S905 to the time table storage unit 62 of the data processing device 106 and the purport of controlling the pumps 102A and 102B using the pump control unit 63 of the data processing device 106 based on the time table is set (S907). That is, the time table used when the pumps are controlled by the pump control unit 63 is switched to the time table manipulated in S905 from another time table. Subsequently, when the sample measurement is started by the operator, the data processing device 106 controls the pumps 102A and 102B according to the time table manipulated in S905 (S908). In this manner, the measurement in the device A is reproduced in the device B and the measurement results which are the same as those of the device A can be obtained in the device B.

Next, a method of acquiring elution responses of respective liquid chromatographs will be described. First, as a hardware configuration when the elution response is acquired, a configuration in which the detector 105 is directly connected to the outlet of the auto sampler 103 to which the column 207 is normally connected can be exemplified. The elution response can be obtained by measuring the absorbance of the eluent sent from the pumps 102A and 102B using the detector 105. In addition, the detector 105 may be connected to the outlet of the auto sampler 103 through the column 207 as in the normal configuration. In the latter case, a resistance tube in place of the column 207 is connected to the outlet of the auto sampler 103, the detector 105 is connected to the resistance tube, and the elution response may be acquired. Moreover, from a viewpoint of acquiring the elution response, it is preferable that the resistance pipe and the column have a low capacity. In addition, the case where the sample injection unit is the auto sampler 103 has been described here, but the sample injection unit may be a manual injector.

Further, from a viewpoint of prioritizing utilization of an existing device, the case where an eluent discharged from the sample injection unit (auto sampler 103) is detected has been described here, but an outlet which is freely opened and closed to discharge an eluent to the outside of the liquid chromatograph may be separately provided and a detecting device capable of measuring the absorbance similar to the detector 105 may be attached to the outlet.

Figure 10:
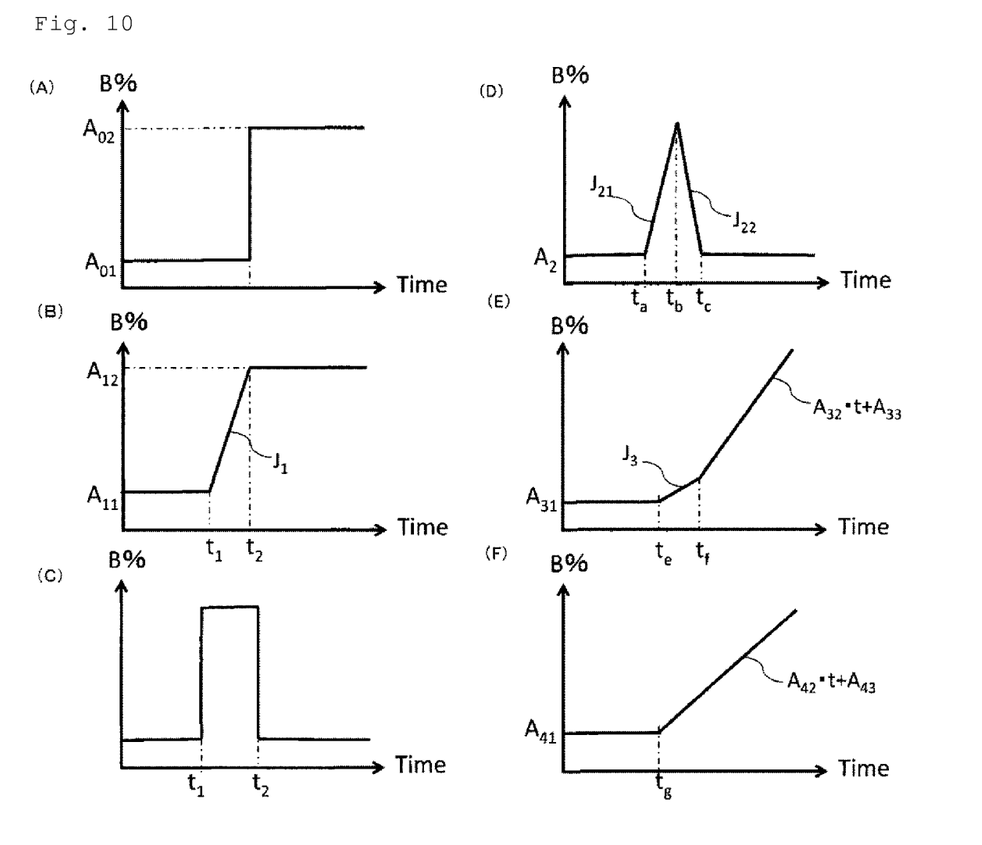
FIG. 10 illustrates examples of command values output to a pump when an elution response of a liquid chromatograph is acquired.

Next, specific examples of the command value output to the pumps 102 (pumps 102A and 102B) when the elution response is acquired will be described. The command value regulates the control of the pumps 102 (102A and 102B) at the micro time of an order of several milliseconds to several seconds and there are various ones. FIG. 10 is a diagram illustrating an example of the command value output to the pumps (pumps 102A and 102B) when the elution response of the liquid chromatograph is acquired. Here, the variation in a case where the mixing ratio of two types of eluents to be pumped up by the pumps 102A and 102B are changed with time while the total flow rate of the two types of eluents 201A and 201B is maintained to be constant will be described with reference to FIG. 10. The elution response can be acquired from the actual elution profile (for example, the gradient curve) to be obtained by detecting the absorbance of the eluent sent from the pumps 102 to which the command value is input.

First, as an example of the command value, a command value that step-functionally changes the mixing ratio of two types of eluents to be pumped by the pumps 102A and 102B with time while the total flow rate of two types of the eluents (eluents 201A and 201B) is maintained to be constant as illustrated in (A) of FIG. 10 (or the elution response curve display unit 91 of FIG. 8) can be exemplified. As the method of manipulating the elution response, a method of manipulating the elution response by normalizing an observation value at the time when the observation value after an eluent is switched on the actual gradient curve enters a steady state is set as 1 and manipulating a difference or a delta of the gradient curve after normalization can be exemplified.

Further, as an example of the command value, a command value of switching the mixing ratio of two types of eluents (eluents 201A and 201B) based on $H_1(t)$ which is a function of the time t regulated by the following equation (5) can be exemplified (see FIG. 10(B)). As the method of manipulating the elution response, a method of manipulating the elution response by measuring the gradient curve obtained when the command value is input to the pumps 102A and 102B and manipulating a difference or a delta of the gradient curve can be exemplified. In the equation (5), $A_{11}$ and $A_{12}$ are constants and a relationship of "$A_{12} > A_{11}$" is satisfied. Further, it is preferable that a difference between $t_2$ and $t_1$ is in the range of milliseconds to seconds. In addition, $H_1(t)$ is continuous in a case of "$t=t_1$, $t_2$" as a boundary condition. That is, a relationship of "$J_1(t_1) = A_{11}$" is satisfied in a case of "$t=t_1$" and a relationship of "$J_1(t_2) = A_{12}$" is satisfied in a case of "$t=t_2$." $J_1(t)$ is a monotonically increasing function of the time t and examples thereof include a polynomial, an exponential function, and a function combining these. In addition, when a relationship of "$A_{12} < A_{11}$" is satisfied, $J_1(t)$ is set as a monotonically decreasing function.

[Math. 5]

$$H_1(t) = \begin{cases} A_{12} & (t \geq t_2) \\ J_1(t) & (t_2 \geq t \geq t_1) \quad t_1 \neq t_2 \\ A_{11} & (t_1 \geq t) \end{cases} \quad \text{Equation (5)}$$

Moreover, as an example of the command value, a command value of switching the mixing ratio of two types of eluents (eluents 201A and 201B) as in a case of a boxcar function can be exemplified (see FIG. 10(C)). As the method of manipulating the elution response, a method of manipulating the elution response by manipulating the area value of a peak on the gradient curve to be actually detected by a detector and normalizing the gradient curve such that the area value of the peak becomes 1 can be exemplified. The elution response may be the normalized gradient curve. It is preferable that the width of the boxcar function is in the range of milliseconds to seconds.

Further, as an example of the command value, a command value of switching the mixing ratio of two types of eluents (eluents 201A and 201B) based on $H_2(t)$ regulated by the following equation (6) can be exemplified (see FIG. 10(D)). In the equation (6), it is preferable that a difference between $t_b$ and $t_a$ and a difference between $t_c$ and $t_b$ are respectively in the range of milliseconds to seconds. $H_2(t)$ is continuous in a case of "$t=t_a$, $t_b$, $t_c$" as a boundary condition. That is, a relationship of "$J_{21}(t_a) = A_2$" is satisfied in a case of "$t=t_a$," a relationship of "$J_{21}(t_b) = J_{22}(t_b)$" is satisfied in a case of "$t=t_b$," and a relationship of "$J_{22}(t_c) = A_2$" is satisfied in a case of "$t=t_c$." $J_{21}(t)$ is a monotonically increasing function and examples thereof include a monotonically increasing polynomial, a monotonically increasing exponential function, and a function combining these. $J_{22}(t)$ is a monotonically decreasing function and examples thereof include a monotonically decreasing polynomial, a monotonically decreasing exponential function, and a function combining these.

[Math. 6]

$$H_2(t) = \begin{cases} A_2 & (t \geq t_c) \\ J_{22}(t) & (t_c \geq t \geq t_b) \\ J_{21}(t) & (t_b \geq t \geq t_a) \\ A_2 & (t \geq t_a) \end{cases} \quad t_a \neq t_b, t_b \neq t_c \quad \text{Equation (6)}$$

Moreover, as an example of the command value, a command value of switching the mixing ratio of two types of eluents (eluents 201A and 201B) based on $H_3(t)$ regulated by the following equation (7) can be exemplified (see FIG. 10(E)). The elution response at this time may be determined by calculating a second order differential (or second order delta) of the gradient curve to be actually detected by a detector and normalizing the area of the peak to 1. In the equation (7), $A_{31}$, $A_{32}$, and $A_{33}$ respectively represent a positive constant. It is preferable that a difference between $t_f$ and $t_e$ is in the range of milliseconds to seconds. $H_3(t)$ is continuous in a case of "$t=t_e$, $t_f$" as a boundary condition. That is, a relationship of "$J_3(t_e) = A_{31}$" is satisfied in a case of "$t=t_e$" and a relationship of "$J_3(t_f) = A_{32} \cdot t_f + A_{33}$" is satisfied in a case of "$t=t_f$." $J_3(t)$ is a monotonically increasing function and examples thereof include a polynomial, an exponential function, and a function combining these.

[Math. 7]

$$H_3(t) = \begin{cases} A_{32} \cdot t + A_{33} & (t \geq t_f) \\ J_3(t) & (t_f \geq t \geq t_e) \quad t_e \neq t_f \\ A_{31} & (t_e \geq t) \end{cases} \quad \text{Equation (7)}$$

Moreover, as an example of the command value, a command value of switching the mixing ratio of two types of eluents (eluents 201A and 201B) based on $H_4(t)$ regulated by the following equation (8) can be exemplified (see FIG. 10(F)). The elution response at this time may be determined by calculating a second order differential (or second order delta) of the gradient curve to be actually detected by a detector and normalizing the area of the peak to 1. In the equation (8), $A_{41}$, $A_{42}$, and $A_{43}$ respectively represent a positive constant. $H_4(t)$ is continuous in a case of "$t=t_g$" as a boundary condition. That is, a relationship of "$H_4(t_g) = A_{42} \cdot t_g + A_{43}$" is satisfied in a case of "$t=t_g$"

[Math. 8]

$$H_4(t) = \begin{cases} A_{42} \cdot T + A_{43} & (t \geq t_g) \\ A_{41} & (t_g \geq t) \end{cases} \quad \text{Equation (8)}$$

In a case of improving the S/N ratio of the elution response (gradient curve) to be actually obtained through absorbance measurement using the detector 105, it is preferable to use a smoothing process according to a moving-average method, a Savitzky-Golay method, a Kawata-Minami method, a frequency domain method, or a method of combining these. Further, the same smoothing process may be performed on the difference (S102 and S904) among elution responses of respective devices or the converted time table (S103 and S905).

Further, in a case where data sampling periods are adjusted to be the same among respective elution responses at the time of manipulating the difference (Trans(t)) among elution responses of respective devices, it is preferable to use interpolation such as linear interpolation, spline interpolation, polynomial interpolation, continued fraction interpolation, or a trigonometric function.

Meanwhile, a known technique (reference: "*Waveform Data Processing for Scientific Measurement*" edited by Shigeo Minami, CQ Publishing Co., Ltd., April, 1986) can be used as the method of manipulating the difference (Trans (t)) among the elution responses of respective devices using deconvolution. In addition, the method of calculating the deconvolution, a method of assuming the shape of the function of Trans(t) in advance and determining the function of Trans (t) so as to satisfy each equation (for example, the equation (3) or the equation (4)) may be used. The function of Trans(t) at this time is calculated from all functions (equations (9) to (13)) shown below or several convolutions of the functions (equations (9) to (13)) shown below. Further, the functions shown below may be convoluted after the area value is normalized.

[Math. 9]

$$\text{Gaussian}(t) = \exp(-t^2/2\sigma^2) \quad \text{(Gaussian)} \quad \text{Equation (9)}$$

[Math. 10]

$$\text{Decay}(t) = \begin{cases} \exp(-t/\tau) & (t \geq 0) \\ 0 & (t < 0) \end{cases} \text{(Exponential function)} \quad \text{Equation (10)}$$

[Math. 11]

$$\text{Shift}(t) = \delta(t - t_p) \; (\text{Dirac delta function}) \quad \text{Equation (11)}$$

[Math. 12]

$$\text{Boxcar}(t) = \begin{cases} 0 & (t \geq t_q, 0 < t) \\ C & (0 \leq t < t_q) \end{cases} \text{(Boxcar function)} \quad \text{Equation (12)}$$

[Math. 13]

$$\text{Alpha}(t) = \begin{cases} -1/(a + at^3) & (t \geq 1/a) \\ 0 & (t < 1/a) \end{cases} \quad \text{Equation (13)}$$

Further, the present invention is not limited to the embodiments described above and various modifications are possible within the range not departing from the scope of the present invention. For example, the present invention is not limited to all configurations described in the embodiments and configurations from which a part thereof is eliminated may be employed. In addition, binomial distribution, Poisson's distribution, geometric distribution, exponential distribution, gamma distribution, or the like may be assumed as the shape of the function of Trans (t) in addition to examples described above.

In addition, some or all of respective configurations and functions and execution processes of the respective configurations related to the above-described liquid chromatograph may be realized using hardware (for example, designing logic of performing each function with an integrated circuit). In addition, the configurations related to the above-described device may be used as a program (software) in which each function related to the configuration of the control device is realized by reading and executing the program with an arithmetic processing device (for example, a CPU) of the data processing device 106 and/or the emulation processing device 107. The information related to the program can be stored in a semiconductor memory (a flash memory, an SSD, or the like), a magnetic storage device (a hard disk drive or the like), or a recording medium (a magnetic disk, an optical disk, or the like).

Further, in the description of the above-described embodiments, control lines or information lines indicate lines necessary for description of the embodiments, but the control lines or the information lines do not necessarily indicate all control lines or all information lines related to a product. Practically, most configurations are connected to one another.

REFERENCE SIGNS LIST

61: Time table input unit
62: Time table storage unit
63: Pump control unit
71: Elution response input unit
72: Elution response storage unit
73: Trans calculation unit
74: Conversion time table manipulating unit
91: Elution response curve display unit
92: Gradient table display unit
93: Gradient curve display unit
94: Device selection button
95: Calculation execution button
96: Setting button
101: Liquid chromatograph unit
102: Pump
103: Auto sampler
104: Column oven
105: Detector
106: Data Processing device
107: Emulation processing device
109: Output device
110: Control unit

The invention claimed is:

1. A liquid chromatograph comprising:
   a liquid chromatograph unit that includes an elution unit sending an eluent to a detecting unit; and
   a control unit that controls a liquid to be sent by the elution unit based on a predetermined time table,
   wherein the control unit stores an elution response of the liquid chromatograph unit which is obtained when a predetermined command value is input to the elution unit and another elution response of another liquid chromatograph which is obtained when the command value is input to another elution unit in another liquid chromatograph,
   wherein the elution response includes an elution profile of an eluent pumped by the elution unit, and
   wherein the control unit converts the time table based on a difference between the elution response of the liquid chromatograph unit and said another elution response of said another liquid chromatograph, such that the elution profile, which is obtained when the elution unit is controlled by the liquid chromatograph unit based on the time table, approaches another elution profile, which is obtained when said another elution unit is controlled by said another liquid chromatograph based on the time table.

2. The liquid chromatograph according to claim 1, wherein the control unit controls the elution unit using the converted time table.

3. The liquid chromatograph according to claim 1, further comprising an outlet to be opened and closed to discharge an eluent flowing when the command value is input to the elution unit to the outside of the liquid chromatograph.

4. The liquid chromatograph according to claim 3,
wherein the outlet is an outlet of a sample injection unit in the liquid chromatograph unit, and
wherein the liquid chromatograph further comprises a detector that is connected to the outlet and detects the elution profile from the elution unit.

5. The liquid chromatograph according to claim 3,
wherein the outlet is an outlet of a sample injection unit in the liquid chromatograph unit, and
wherein the liquid chromatograph further comprises a resistance tube or a column that is connected to the outlet and a detector that is connected to the resistance tube or the column and detects the elution profile from the elution unit.

6. The liquid chromatograph according to claim 1,
wherein the command value step-functionally changes the mixing ratio of a plurality of eluents pumped by the elution unit with time, and
wherein the elution response and said another elution response are processed by measuring a gradient curve obtained when the command value is input to the elution unit.

7. The liquid chromatograph according to claim 1,
wherein the command value changes the mixing ratio of a plurality of eluents pumped by the elution unit based on a function $F_1(t)$ with time (t) (in this case, $C_{11}$ represents a constant, $F_1(t)$ represents continuous distribution, $t_{F1a}$, $t_{F1b}$, and $t_{F1c}$ each represent a constant, $G_{11}(t)$ represents a monotonically increasing function and $G_{12}(t)$ represents a monotonically decreasing function, or $G11(t)$ represents a monotonically decreasing function and $G12(t)$ represents a monotonically increasing function), and
wherein the elution response and said another elution response are processed by measuring a gradient curve obtained when the command value is input to the elution unit, $$F_1(t) = \begin{cases} C_{11} & (t \geq t_{F1c}) \\ G_{12}(t) & (t_{F1c} \geq t \geq t_{F1b}) \\ G_{11}(t) & (t_{F1b} \geq t \geq t_{F1a}) \\ C_{11} & (t \geq t_{F1a}) \end{cases} t_{F1a} \neq t_{F1b}, t_{F1b} \neq t_{F1c}.$$

8. The liquid chromatograph according to claim 1,
wherein the command value step-functionally changes the mixing ratio of a plurality of eluents pumped by the elution unit with time, and
wherein the elution response and said another elution response are processed by measuring a gradient curve obtained when the command value is input to the elution unit and calculating a differential or a delta of the gradient curve.

9. The liquid chromatograph according to claim 1,
wherein the command value changes the mixing ratio of a plurality of eluents pumped by the elution unit based on a function $F_2(t)$ with time (t) (in this case, $C_{21}$ and $C_{22}$ each represent a constant, $F_2(t)$ represents continuous distribution, $t_{F2a}$ and $t_{F2b}$ each represent a constant, $G_{21}(t)$ represents a monotonically increasing function when $C_{21}$ is smaller than $C_{22}$ and $G_{21}(t)$ represents a monotonically decreasing function when $C_{21}$ is greater than $C_{22}$), and
wherein the elution response and said another elution response are processed by measuring a gradient curve obtained when the command value is input to the elution unit and calculating a differential or a delta of the gradient curve, $$F_2(t) = \begin{cases} C_{22} & (t \geq t_{F2b}) \\ G_{21}(t) & (t_{F2b} \geq t \geq t_{F2a}) \\ C_{21} & (t_{F2a} \geq t) \end{cases} t_{F2a} \neq t_{F2b}.$$

10. The liquid chromatograph according to claim 1,
wherein the command value changes the mixing ratio of a plurality of eluents pumped by the elution unit based on a function $F_3(t)$ with time (t) (in this case, $C_{31}$, $C_{32}$, and $C_{33}$ each represent a constant, $F_3(t)$ represents continuous distribution, and $t_{F3a}$ and $t_{F3b}$ each represent a constant), and
wherein the elution response and said another elution response are processed by measuring a gradient curve obtained when the command value is input to the elution unit and calculating a differential or a delta of the gradient curve twice, $$F_3(t) = \begin{cases} C_{32} \cdot t + C_{33} & (t \geq t_{F3a}) \\ C_{31} & (t_{F3a} \geq t) \end{cases}.$$

11. The liquid chromatograph according to claim 1,
wherein the command value changes the mixing ratio of a plurality of eluents pumped by the elution unit based on a function $F_4(t)$ with time (t) (in this case, $C_{41}$, $C_{42}$, and $C_{43}$ each represent a constant, $F_4(t)$ represents continuous distribution, $t_{F4a}$ and $t_{F4b}$ each represent a constant, and $G_{41}(t)$ represents a monotonically increasing function), and
wherein the elution response and said another elution response are processed by measuring a gradient curve obtained when the command value is input to the elution unit and calculating a differential or a delta of the gradient curve twice, $$F_4(t) = \begin{cases} C_{42} \cdot t + C_{43} & (t \geq t_{F4b}) \\ G_{41}(t) & (t_{F4b} \geq t \geq t_{F4a}) \\ C_{41} & (t_{F4a} \geq t) \end{cases} t_{F4a} \neq t_{F4b}.$$

12. The liquid chromatograph according to claim 1, wherein the elution response is normalized based on an area value of a peak on a gradient curve obtained when the command value is input to the elution unit.

13. The liquid chromatograph according to claim 1, wherein the elution response is smoothed using a moving-average method, a Savitzky-Golay method, a Kawata-Minami method, or a frequency domain method.

14. The liquid chromatograph according to claim 1, wherein the difference between the elution response and said another elution response is smoothed using a Savitzky-Golay method, a Kawata-Minami method, or a frequency domain method.

15. The liquid chromatograph according to claim 1, wherein the converted time table is smoothed using a Savitzky-Golay method, a Kawata-Minami method, or a frequency domain method.

16. The liquid chromatograph according to claim 1,
wherein the time table includes time series of control command values to the elution unit and a time change of the elution profile due to the elution unit which is determined in advance.

17. The liquid chromatograph according to claim 16,
wherein the time series of control command values include target values of the elution profile.

18. The liquid chromatograph according to claim 1,
wherein the elution profile includes at least one of a flow rate of the eluent, a pressure of the eluent, or a mixing ratio of respective eluents in a predetermined flow rate in a case where a plurality of eluents are pumped by the elution unit.

19. A liquid chromatograph comprising:
a liquid chromatograph unit that includes an elution unit sending an eluent to a detecting unit; and
a control unit that controls a liquid to be sent by the elution unit based on a predetermined time table;
wherein the control unit stores an elution response of the liquid chromatograph unit which is obtained when a predetermined command value is input to the elution unit and another elution response of another liquid chromatograph which is obtained when the command value is input to another elution unit in another liquid chromatograph;
wherein the command value changes the mixing ratio of a plurality of eluents pumped by the elution unit based on a function $F_1(t)$ with time (t) (in this case, $C_{11}$ represents a constant, $F_1(t)$ represents continuous distribution, $t_{F1a}$, $t_{F1b}$, and $t_{F1c}$ each represent a constant, $G_{11}(t)$ represents a monotonically increasing function and $G_{12}(t)$ represents a monotonically decreasing function, or $G11(t)$ represents a monotonically decreasing function and $G12(t)$ represents a monotonically increasing function); and
wherein the elution response and said another elution response are processed by measuring a gradient curve obtained when the command value is input to the elution unit, $$F_1(t) = \begin{cases} C_{11} & (t \geq t_{F1c}) \\ G_{12}(t) & (t_{F1c} \geq t \geq t_{F1b}) \\ G_{11}(t) & (t_{F1b} \geq t \geq t_{F1a}) \\ C_{11} & (t \geq t_{F1a}) \end{cases} t_{F1a} \neq t_{F1b}, t_{F1b} \neq t_{F1c}.$$

20. A liquid chromatograph comprising:
a liquid chromatograph unit that includes an elution unit sending an eluent to a detecting unit; and
a control unit that controls a liquid to be sent by the elution unit based on a predetermined time table;
wherein the control unit stores an elution response of the liquid chromatograph unit which is obtained when a predetermined command value is input to the elution unit and another elution response of another liquid chromatograph which is obtained when the command value is input to another elution unit in another liquid chromatograph;
wherein the command value changes the mixing ratio of a plurality of eluents pumped by the elution unit based on a function $F_3(t)$ with time (t) (in this case, $C_{31}$, $C_{32}$, and $C_{33}$ each represent a constant, $F_3(t)$ represents continuous distribution, and $t_{F3a}$ and $t_{F3b}$ each represent a constant), and
wherein the elution response and said another elution response are processed by measuring a gradient curve obtained when the command value is input to the elution unit and calculating a differential or a delta of the gradient curve twice, $$F_3(t) = \begin{cases} C_{32} \cdot t + C_{33} & (t \geq t_{F3a}) \\ C_{31} & (t_{F3a} \geq t) \end{cases}.$$

* * * * *